United States Patent [19]
Beranger et al.

[11] Patent Number: 5,142,052
[45] Date of Patent: Aug. 25, 1992

[54] CATIONIC EFFECT-DRIVEN CARBINOL/AMINE REACTION

[75] Inventors: Serge Beranger, Bretigny-Sur-Orge; Bruno Francois, Sainte Genevieve Des Bois, both of France

[73] Assignee: Laboratoires Syntex, Puteaux, France

[21] Appl. No.: 260,965

[22] Filed: Oct. 21, 1988

[30] Foreign Application Priority Data

Apr. 22, 1988 [EP] European Pat. Off. ........ 88303646.9

[51] Int. Cl.$^5$ .................. C07D 241/04; C07D 209/04; C07D 215/38; C07C 209/14
[52] U.S. Cl. .................................... 544/370; 544/373; 544/396; 546/176; 548/504; 548/507; 548/566; 564/389; 564/399; 564/402; 564/393
[58] Field of Search ............... 564/353, 389, 399, 402, 564/393; 544/373, 396, 370; 546/176; 548/342, 504, 507, 566

[56] References Cited

U.S. PATENT DOCUMENTS

| | | | |
|---|---|---|---|
| 2,580,738 | 1/1951 | de Benneville et al. | 548/566 |
| 3,362,956 | 1/1968 | Archer | 260/268 |
| 3,491,098 | 1/1970 | Archer | 260/268 |
| 3,562,278 | 2/1971 | Archer | 544/373 |
| 3,631,043 | 12/1971 | Regnier et al. | 260/250 A |
| 3,649,631 | 3/1972 | Koppe et al. | 260/268 H |
| 3,927,011 | 12/1975 | Nakanishi et al. | 260/296 R |
| 4,022,783 | 3/1977 | Shroff et al. | 260/268 H |
| 4,032,574 | 6/1977 | Kashi et al. | 564/399 |
| 4,229,374 | 10/1980 | Slaugh et al. | 260/563 |
| 4,243,806 | 1/1981 | Raeymaekers et al. | 544/396 |
| 4,404,382 | 9/1983 | Gall | 544/360 |
| 4,409,399 | 10/1983 | Swift et al. | 564/473 |
| 4,721,810 | 1/1988 | Hargis | 564/399 |

FOREIGN PATENT DOCUMENTS

| | | |
|---|---|---|
| 0054974 | 6/1982 | European Pat. Off. . |
| 0072623 | 2/1983 | European Pat. Off. . |
| 2022073 | 5/1979 | United Kingdom . |
| 1551993 | 9/1979 | United Kingdom . |

OTHER PUBLICATIONS

Hackh's Chem. Dict. Fourth Ed. (McGraw-Hill Book Co.) p. 27 (1969).
March, Adv. Org. Chem. Second Ed. (McGraw-Hill Book Co.) p. 325 (1977).
Grant & Hackh's Chem. Dict. Fifth Ed. (McGraw-Hill Book Co.) p. 151.
Shibahara et al., Chem. Abs. vol. 75 No. 15 entry #98463z (1971).
Kozlov et al., Chem. Abs. vol. 78, No. 14 entry #88985u (1973).

Primary Examiner—Robert T. Bond
Assistant Examiner—E. C. Ward
Attorney, Agent, or Firm—David A. Lowin; Tom M. Moran

[57] ABSTRACT

Aryl- and heterocyclic-methanamines are prepared by reacting a hydroxy-aryl carbinol or a heterocyclic carbinol with a primary or a secondary amine in the presence of a cationic effect reagent.

23 Claims, No Drawings

CATIONIC EFFECT-DRIVEN CARBINOL/AMINE REACTION

BACKGROUND OF THE INVENTION

1. Cross-reference to Related Applications

This application is related to European Patent Application 88.303646.9, filed Apr. 22, 1988, incorporated herein by reference, and claims priority therefrom. Cross-reference is also made to U.S. Ser. No. 042,181, filed Apr. 24, 1987 now U.S. Pat. No. 4,829,065, issued May 9, 1989 and to its continuation-in-part U.S. Ser. No. 260,969, filed contemporaneously herewith now U.S. Pat. No. 5,043,447 and both incorporated herein by reference, where preparation of 1-diphenylmethyl-4-[(2-(4-methylphenyl)-5-methyl-1H-imidazol-4-yl)methyl]piperazine (a compound within the scope of compounds made by the present invention) and its uses are taught.

2. Field of the Invention

The present invention relates to synthetic chemical reactions between alcohols and primary or secondary amines, particularly in the preparation of certain aryl- and heterocyclic-methanamines. The invention is also directed to the chemical compositions, particularly pharmaceutical active agents, and amphoteric phenolamines used as intermediates in the photographic, color, phytosanitary and pharmaceutical industries.

BACKGROUND INFORMATION

The synthetic reactions employed in the past for making aryl- and heterocyclic-methanamines suffered from several disadvantages. Often, these reactions were quite complicated, involving many steps (typically including protection and de-protection). At industrial scale, they entailed the manipulation of large quantities of hazardous chemicals (e.g., NaOH, hydrogen gas, thionyl chloride), giving rise to problems of corrosion, toxicity, explosion, smell and environmental considerations. Additionally, the reagents used therein (e.g., palladium catalysts) were often expensive.

A typical synthesis of hydroxy-benzylamines entailed the following steps:

Step 1 - Protection

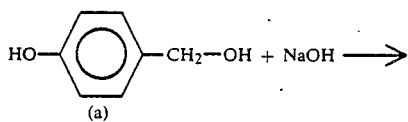

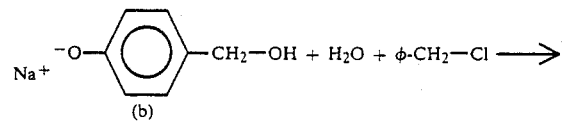

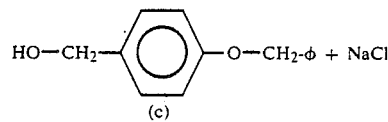

Step 2 - Halogenation

-continued

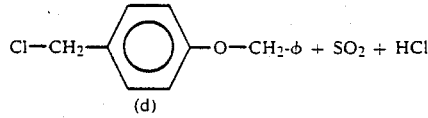

Step 3 - Alkylation

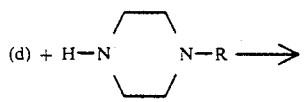

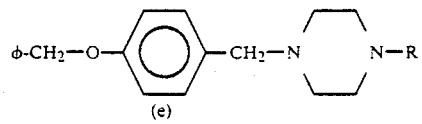

Step 4 - Deprotection

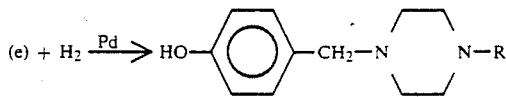

Similarly, a typical synthesis of heterocyclic methanamines entailed the following steps:

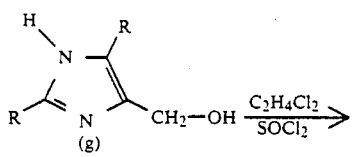

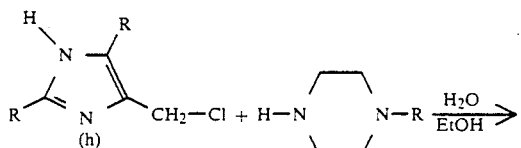

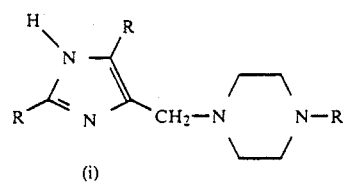

Thus, in view of the disadvantages of the prior synthetic processes, it has remained desired to provide a process for the synthesis of aryl- and heterocyclic-methanamines, which involves fewer and less complicated steps, employs safer and less expensive reagents, and produces high yields in less time. It has further been desired to provide such a process, which can be carried out in a single reaction vessel. The synthetic processes of the present invention provide such a reaction and satisfy the foregoing requirements.

SUMMARY OF THE INVENTION

Aryl- and heterocyclic-methanamines represented by Formula I:

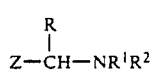

wherein:
Z is a group of the formula HO-Ar- where Ar is phenyl, substituted phenyl, or naphthyl, or
Z is a five to seven membered optionally substituted heterocyclic group of the formula:

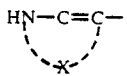

where X is a succession of one or two groups selected from —C=C—, —C=N—, —C=C—C— and —C=N—C—, or
Z is a condensed heterocyclic group selected from optionally substituted indole and optionally substituted quinoline;
R is a substituent giving a global electron donor effect, selected from the group including: hydrogen, lower alkyl, phenyl, substituted phenyl, or naphthyl;
$R^1$ is hydrogen, alkyl, phenyl, substituted phenyl, or naphthyl;
$R^2$ is hydrogen, alkyl, phenyl, substituted phenyl, or naphthyl;
or $NR^1R^2$ taken together forms a heterocycle where $R^1$ and $R^2$ together are lower alkylene of four to six carbon atoms, or lower alkylene of three to five carbon atoms plus one member that is —O—, —S— or

where $R^3$ is hydrogen, lower alkyl of one to five carbon atoms, aryl, arylalkyl or diarylalkyl;
are prepared by reacting a carbinol of the formula:

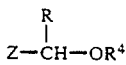

where $R^4$ is hydrogen or alkyl; with a primary or secondary amine of the formula:

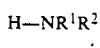

in the presence of a cationic effect reagent. The cationic effect reagent is a metal hydroxide and a metal salt.

DETAILED DESCRIPTION OF THE INVENTION

Definitions and General Parameters

The following definitions are set forth to illustrate and define the meaning and scope of the various terms used to described the invention herein.

As used herein, the term "alkyl" refers to a fully saturated monovalent radical containing only carbon and hydrogen, and which may be a branched or straight chain radical. This term is further exemplified by radicals such as methyl, ethyl, t-butyl, pentyl, pivalyl, and heptyl.

The term "cycloalkyl" refers to carbocyclic radicals, such as cyclopropylmethyl and adamantyl.

The term "lower alkyl" refers to a branched or straight chain monovalent alkyl radical of one to six carbon atoms. This term is further exemplified by such radicals as methyl, ethyl, n-propyl, isopropyl, n-butyl, t-butyl, i-butyl (or 2-methylpropyl), i-amyl, n-amyl, and hexyl.

The term "cyclic lower alkyl" refers to carbocyclic radicals of three to six carbon atoms, such as cyclopropylmethyl.

The term "alkylene" refers to a fully saturated divalent radical containing only carbon and hydrogen, and which may be a branched or straight chain radical. This term is further exemplified by radicals such as methylene, ethylene, n-propylene, t-butylene, i-pentylene, and n-heptylene.

The term "lower alkylene" refers to a divalent alkyl radical of one to six carbon atoms. This term is further exemplified by such radicals as methylene, ethylene, n-propylene, i-propylene, n-butylene, t-butylene, i-butylene (or 2-methylpropylene), isoamylene, pentylene, and n-hexylene.

The term "aryl" or "Ar" refers to a monovalent unsaturated aromatic carbocyclic radical having a single ring (e.g., phenyl) or two condensed rings (e.g., naphthyl), which can optionally be mono-, di- or tri-substituted, independently, with hydroxy, lower alkyl, lower alkoxy, chloro, and/or fluoro.

As used herein, the term "halo" refers to fluoro, bromo, chloro and iodo.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution.

As used herein, the terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

Unless specified to the contrary, the reactions described herein take place at atmospheric pressure over a temperature range from about 10° C. to about 100° C., more preferably from about 40° C. to about 80° C., and most preferably at the reflux temperature of the reaction mixture.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

Synthesis of the Compounds of Formula I

As used in the Reaction Schemes, the substituents Z, Ar, X, $R^1$, $R^2$, $R^3$, $R^4$ and $NR^1R^2$, are the same as described in the Summary of the Invention.

Reaction Scheme 1

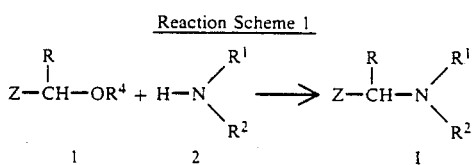

Referring to Reaction Scheme 1, approximately equimolar equivalents of a carbinol (Formula 1) and an amine (Formula 2) are added to a reaction vessel in the presence of a cationic effect reagent. The reaction takes place in a medium in which said starting materials are soluble, but in which said final product (Formula I) is insoluble, at a temperature from about 20° C. to about 140° C., preferably at the reflux temperature of the reaction mixture, for a time from about 1 to about 48 hours, preferably 4 to 24 hours.

The Carbinols

The carbinols useful in the reactions of the present invention must have a conjugate structure with an acidic character. These two characteristics are required for the carbocation formation in the presence of the cationic effect reagent.

Hydroxy-aryl carbinols

The starting materials of Formula 1 where Z is a group of the formula HO—Ar—, include the compounds where Ar is phenyl, substituted phenyl, or naphthyl. Preferred hydroxy-aryl carbinols include hydroxy-phenyl carbinols (e.g., 2-hydroxybenzyl alcohol, 3-hydroxybenzyl alcohol, 4-hydroxybenzyl alcohol, 3-hydroxy-4-methoxybenzyl alcohol and 4-hydroxy-3-methoxybenzyl alcohol, commercially available from Aldrich Chemical of Milwaukee, Wis., and 4-hydroxy-3,5-dimethoxybenzyl alcohol, commercially available from Lancaster Synthesis Ltd. of Wyndham, N.H.) and 6-hydroxy-2-naphthyl-carbinols (e.g., 6-hydroxy-2-naphthylenemethanol, which can be prepared from the corresponding aldehyde by methods known to those skilled in the art).

Heterocyclic carbinols

The starting materials of Formula 1 where Z is a five to seven membered heterocyclic group of the formula:

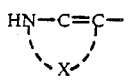

optionally substituted at any available location on the heterocycle, include the compounds where X is a succession of one or two groups selected from —C=C—, —C=N—, —C=C—C— and —C=N—C—.

Preferred heterocyclic and condensed heterocyclic carbinols include 2-imidazolyl-carbinols [e.g., 4-(hydroxymethyl)imidazole], 3-indolyl-carbinols (e.g., 3-indolemethanol), 4-quinolyl-carbinols (e.g., 2,4-quinolinediol) and 4-pyrazolyl-carbinols (e.g., 4-pyrazolemethanol), each of the foregoing examples being commercially available from Aldrich.

The Amines

Primary and Secondary Amines

The primary and secondary amines useful in the reactions of the present invention include:
primary aliphatic amines such as alkylamines (e.g., propyl, n-butyl, t-butyl, and hexyl) and cycloalkylamines (e.g., cyclopentyl, cyclohexyl-amine, and adamantadine);
secondary aliphatic amines (e.g., diethylamine, di-isopropylamine, dibutylamine, piperidine);
arylamines (e.g., benzylamine),
primary aralkylamines (e.g., phenethylamine); and
secondary aralkylamines (e.g., N-methyl-phenethylamine),
each of the foregoing examples being commercially available, for example, from Aldrich.

Heterocyclic Amines

Heterocyclic amines useful in the reactions of the present invention include:
optionally substituted piperazines [e.g., piperazine, phenylpiperazine, 1-(2-methoxyphenyl)piperazine, and 1-(4-chlorophenyl)piperazine), commercially available from Aldrich, and
diphenylmethyl-piperazines, prepared, e.g., by the procedures of Hamlin et al., *J. Am. Chem. Soc.*, 71, 31 (1949) or Cheeseman, *J. Chem. Soc.*, 115-123 (1975)].

The Cationic Effect Reagent

The cationic effect is induced by a combination of a metal hydroxide and a metal salt. The metal hydroxide is preferably an alkaline metal hydroxide (most preferably potassium or sodium hydroxide). The metal salt is preferably a metal halide or a metal perchlorate (more preferably a lithium halide or a lithium percholorate, and most preferably lithium bromide).

The ratio of metal hydroxide to salt can vary from 1:20 to 20:1 on a molar scale. It is preferred that the hydroxide be used in a smaller quantity than the salt, most preferably about 0.1 molar equivalents of alkaline hydroxide to 1.0 molar equivalent of metal salt.

The Reaction Medium

The reaction medium can be heterogeneous or homogeneous.

Heterogeneous reaction media include, e.g., a mixture of an aqueous solvent (such as water) and either an aromatic solvent (such as benzene, toluene or xylene) or an aliphatic solvent (such as dichloromethane and dichloroethane), preferably in a ratio from 1:10 to 10:1 v/v. A phase transfer catalyst [e.g., 3-octyl ammonium chloride ("Aliquat 366") or tetrabutyl ammonium bromide ("TBAB")] is preferably used when employing heterogeneous media.

Homogeneous reaction media include, e.g., hydroalcoholic mixtures and organic solvents. Non-aqueous homogeneous reaction media is preferred, especially toluene.

Preparation of the Salts of Formula I

Once the compounds of Formula I have been prepared according to the process of the present invention, their pharmaceutically acceptable salts may be prepared according to methods commonly employed in the art.

Compounds Made by the Present Invention

Compounds prepared by the above-described preferred process of the invention may be identified (e.g., using mass spectroscopy, NMR spectroscopy, or preferably, atomic absorption spectroscopy) by the presence of a slight, but detectable amount of a metal salt, e.g., a lithium compound used in the process as a reagent (e.g., LiBr) or produced in it as a side product (e.g., LiOH).

While it is well known that pharmaceuticals must meet pharmacopoeia standards before approval and/or marketing, and that synthetic reagents or side products should not exceed the limits prescribed by pharmacopoeia standards, final compounds prepared by a process of the present invention may have minor, but detectable, amounts of such materials present. It is important to monitor the purity pharmaceutical compounds for the presence of such materials, which presence is additionally disclosed as a method of detecting use of a process of the invention.

Preferred Processes and Last Steps

Aryl- and heterocyclic-methanamines are prepared by reacting a hydroxy-aryl carbinol or a heterocyclic carbinol with a primary or a secondary amine in the presence of a cationic effect reagent.

Particularly preferred as the cationic effect reagent are potassium or sodium hydroxide, and a lithium halide or a lithium perchlorate, most preferably lithium bromide.

Preferred Compound

A preferred compound made by the process of the present invention is 1-diphenylmethyl-4-[(2-(-4-methylphenyl)-5-methyl-1H-imidazol-4-yl)methyl]piperazine.

EXAMPLES

The following examples are given to enable those skilled in the art to more clearly understand and to practice the present invention. They should not be considered as limiting the scope of the invention, but merely as being illustrative and representative thereof.

EXAMPLE 1

1-(2-Methoxyphenyl)-4-[(4-hydroxyphenyl)methyl]piperazine

4-Hydroxyphenyl methanol (124 g, 1 mole) and 192 g (1 mole) of 1-(2-methoxyphenyl)piperazine, together with 56 g (1 mole) of potassium hydroxide and 8.7 g (0.1 mole) of lithium bromide and 32.2 g (0.1 mole) of Aliquat 366 were dissolved in a mixture of 1 liter of toluene and 1 liter of water. The reaction mixture was refluxed for 24 hours, and then allowed to cool to room temperature. The organic layer was decanted and extracted twice with 500 ml of a 10% sodium hydroxide solution. The basic aqueous liquor was treated with ammonium acetate to provoke precipitation of the desired product. After filtration and drying under vacuum overnight at 50° C., 167 g (0.56 mole, 56% yield) of the title product was obtained as small white leaflets melting at 172° C.

EXAMPLE 2

1-(2-Methoxyphenyl)-4-[(4-hydroxyphenyl)methyl]piperazine

2A. Formula I Where Z is 4-Hydroxyphenyl, —N—$R^1R^2$ is 1-(2-methoxyphenyl)piperazine, and R is Hydrogen One mole of 4-hydroxyphenyl methanol (124 g) and 192 g (2 moles) of 1-(2-methoxyphenyl)piperazine were dissolved in 1.5 liters of toluene. One mole (87 g) of lithium bromide and 0.1 mole (5.6 g) of potassium hydroxide were added portionwise, under stirring, and the reaction medium was heated to reflux for 5 hours. The reaction mixture was then allowed to cool to room temperature, and extracted twice with 500 ml of a 1N sodium hydroxide. The basic aqueous liquor was washed with 300 ml of toluene and then acidified to pH 7 with acetic acid to provoke precipitation of the desired product. The precipitate thus obtained was filtered off and then recrystallized from isopropanol, giving 238.4 g (0.80 mole, 80% yield) of the title product, melting at 172° C.

2B. Formula I Varying Z

Similarly, following the procedure of Part A above, but replacing 4-hydroxyphenyl methanol with:
2-hydroxybenzyl alcohol;
3-hydroxybenzyl alcohol;
4-hydroxybenzyl alcohol;
4-hydroxy-3-methoxybenzyl alcohol;
4-hydroxy-3-methoxybenzyl alcohol;
4-hydroxy-3,5-dimethoxybenzyl alcohol;
6-hydroxy-2-naphthylenemethanol;
4-(hydroxymethyl)imidazole;
3-indolemethanol;
4-pyrazolemethanol;
1-(4-hydroxyphenyl)-1-propanol; and
1-(4-hydroxyphenyl)benzyl alcohol,
there is obtained:
1-(2-methoxyphenyl)-4-(2-hydroxybenzyl)piperazine
1-(2-methoxyphenyl)-4-(3-hydroxybenzyl)piperazine;
1-(2-methoxyphenyl)-4-(4-hydroxybenzyl)piperazine;
1-(2-methoxyphenyl)-4-(4-hydroxy-3-methoxybenzyl)piperazine;
1-(2-methoxyphenyl)-4-(4-hydroxy-3-methoxybenzyl)piperazine;
1-(2-methoxyphenyl)-4-(4-hydroxy-3,5-dimethoxybenzyl)piperazine;
1-(2-methoxyphenyl)-4-[(6-hydroxy-2-naphthyl)methyl]piperazine;
1-(2-methoxyphenyl)-4-[(4-imidazolyl)methyl]piperazine;
1-(2-methoxyphenyl)-4-[(3-indole)methyl]piperazine;
1-(2-methoxyphenyl)-4-[(4-pyrazole)methyl]piperazine;
1-(2-methoxyphenyl)-4-[(4-hydroxyphenyl)-1-propyl]piperazine; and
1-(2-methoxyphenyl)-4-[(4-hydroxyphenyl)phenylmethyl]piperazine.

2C. Formula I Varying -$NR^1R^2$

Similarly, following the procedure of Part A above, but replacing 1-(2-methoxyphenyl)piperazine with:
propylamine;
n-butylamine;
t-butylamine;
hexylamine;
cyclopentylamine;

cyclohexylamine;
adamantadine;
diethylamine;
di-isopropylamine;
dibutylamine;
piperidine;
benzylamine;
phenethylamine;
N-methyl-phenethylamine;
piperazine;
phenylpiperazine; and
1-(4-chlorophenyl)piperazine),
there is obtained:
N-propyl-N-[(4-hydroxyphenyl)methyl]amine;
N-n-butyl-N-[(4-hydroxyphenyl)methyl]amine;
N-t-butyl-N-[(4-hydroxyphenyl)methyl]amine;
N-hexyl-N-[(4-hydroxyphenyl)methyl]amine;
N-cyclopentyl-N-[(4-hydroxyphenyl)methyl]amine;
N-cyclohexyl-N-[(4-hydroxyphenyl)methyl]amine;
N-adamantyl-N-[(4-hydroxyphenyl)methyl]amine;
N-diethyl-N-[(4-hydroxyphenyl)methyl]amine;
N-di-isopropyl-N-[(4-hydroxyphenyl)methyl]amine;
N-dibutyl-N-[(4-hydroxyphenyl)methyl]amine;
N-[(4-hydroxyphenyl)methyl]piperidine;
N-benzyl-N-[(4-hydroxyphenyl)methyl]amine;
N-phenethyl-N-[(4-hydroxyphenyl)methyl]amine;
N-methyl-N-phenethyl-N-[(4-hydroxyphenyl)methyl]amine;
1-[(4-hydroxyphenyl)methyl]piperazine alone or mixed with 1,4-di-[(4-hydroxyphenyl)methyl]piperazine;
1-phenyl-4-[(4-hydroxyphenyl)methyl]piperazine; and
1-(4-chlorophenyl)-4-[(4-hydroxyphenyl)methyl]piperazine).

2D. Formula I Varying -NR¹R²

Similarly, following the procedure of Part A above, but replacing 1-(2-methoxyphenyl)piperazine with:
N-(diphenylmethyl)piperazine;
N-[di-(2-methylphenyl)methyl]piperazine;
N-[di-(3-methylphenyl)methyl]piperazine;
N-[di-(4-methylphenyl)methyl]piperazine;
N-[di-(2-t-butylphenyl)methyl]piperazine;
N-[di-(3-t-butylphenyl)methyl]piperazine;
N-[di-(4-t-butylphenyl)methyl]piperazine;
N-[di-(2-methoxyphenyl)methyl]piperazine;
N-[di-(3-methoxyphenyl)methyl]piperazine;
N-[di-(4-methoxyphenyl)methyl]piperazine;
N-[di-(2-chlorophenyl)methyl]piperazine;
N-[di-(3-chlorophenyl)methyl]piperazine;
N-[di-(4-chlorophenyl)methyl]piperazine;
N-[di-(4-fluorophenyl)methyl]piperazine;
N-benzylpiperazine;
N-[1-(4-chlorophenyl)-1-(phenyl)methyl]piperazine;
N-(2,2-diphenylethyl)piperazine;
N-[3-(phenyl)-3-(4-methoxyphenyl)propyl]piperazine; and
N-(4,4-diphenylbutyl)piperazine,
there is obtained:
1-(diphenylmethyl)-4-[(4-hydroxyphenyl)methyl]piperazine;
1-[di-(2-methylphenyl)methyl]-4-[(4-hydroxyphenyl)methyl]piperazine;
1-[di-(3-methylphenyl)methyl]-4-[(4-hydroxyphenyl)methyl]piperazine;
1-[di-(4-methylphenyl)methyl]-4-[(4-hydroxyphenyl)methyl]piperazine;
1-[di-(2-t-butylphenyl)methyl]-4-[(4-hydroxyphenyl)methyl]piperazine;
1-[di-(3-t-butylphenyl)methyl]-4-[(4-hydroxyphenyl)methyl]piperazine;
1-[di-(4-t-butylphenyl)methyl]-4-[(4-hydroxyphenyl)methyl]piperazine;
1-[di-(2-methoxyphenyl)methyl]-4-[(4-hydroxyphenyl)methyl]piperazine;
1-[di-(3-methoxyphenyl)methyl]-4-[(4-hydroxyphenyl)methyl]piperazine;
1-[di-(4-methoxyphenyl)methyl]-4-[(4-hydroxyphenyl)methyl]piperazine;
1-[di-(2-chlorophenyl)methyl]-4-[(4-hydroxyphenyl)methyl]piperazine;
1-[di-(3-chlorophenyl)methyl]-4-[(4-hydroxyphenyl)methyl]piperazine;
1-[di-(4-chlorophenyl)methyl]-4-[(4-hydroxyphenyl)methyl]piperazine;
1-[di-(4-fluorophenyl)methyl]-4-[(4-hydroxyphenyl)methyl]piperazine;
1-benzyl-4-[(4-hydroxyphenyl)methyl]piperazine;
1-[1-(4-chlorophenyl)-1-(phenyl)methyl]-4-[(4-hydroxyphenyl)methyl]piperazine;
1-(2,2-diphenylethyl)-4-[(4-hydroxyphenyl)methyl]piperazine;
1-[3-(phenyl)-3-(4-methoxyphenyl)propyl]-4-[(4-hydroxyphenyl)methyl]piperazine; and
1-(4,4-diphenylbutyl)-4-[(4-hydroxyphenyl)methyl]piperazine.

EXAMPLE 3

1-Diphenylmethyl-4-[(2-(-4-methylphenyl)-5-methyl-1 H-imidazol-4-yl)methyl]piperazine

3A. Formula I Where Z is 4-[2-(-4-Methylphenyl)-5-methyl-1H-imadazole, -N-R¹R² is Diphenylmethylpiperazine, and R is Hydrogen One mole of 4-hydroxymethyl-2-(4-methylpheny)-5-methyl-1H-imidazole (202 g) was dissolved in 2 liters of 95% ethanol, then 252 g (1 mole) of N-(diphenylmethyl)piperazine was added portionwise. This was followed by the addition of 1 liter of water, 60 g (1.5 mole) of sodium hydroxide (as 12N solution) and 8.7 g (0.1 mole) of lithium bromide. The reaction medium was refluxed for 5 hours, allowed to cool to room temperature, and was stirred overnight. The precipitate that formed was filtered and purified by reslurrying from 1.2 liters of an ethanol-water mixture (60/40) to produce the 383.6 g of the title compound (0.88 mole, 88% yield), having a melting point of 238° C.

3B. Formula I Varying Z

Similarly, following the procedure of Part A above, but replacing 4-hydroxymethyl-2-(4-methylphenyl)-5-methyl-1H-imidazole with:
2-hydroxybenzyl alcohol;
3-hydroxybenzyl alcohol;
4-hydroxybenzyl alcohol;
4-hydroxy-3-methoxybenzyl alcohol;
4-hydroxy-3-methoxybenzyl alcohol;
4-hydroxy-3,5-dimethoxybenzyl alcohol;
6-hydroxy-2-naphthylenemethanol;
4-(hydroxymethyl)imidazole;
3-indolemethanol; and
4-pyrazolemethanol,
there is obtained:
1-diphenylmethyl-4-(2-hydroxybenzyl)piperazine
1-diphenylmethyl-4-(3-hydroxybenzyl)piperazine;
1-diphenylmethyl-4-(4-hydroxybenzyl)piperazine;

1-diphenylmethyl-4-(4-hydroxy-3-methoxybenzyl)piperazine;
1-diphenylmethyl-4-(4-hydroxy-3-methoxybenzyl)piperazine;
1-diphenylmethyl-4-(4-hydroxy-3,5-dimethoxybenzyl)piperazine;
1-diphenylmethyl-4-[(6-hydroxy-2-naphthyl)methyl]piperazine;
1-diphenylmethyl-4-[(4-imidazolyl)methyl]piperazine;
1-diphenylmethyl-4-[(3-indole)methyl]piperazine; and
1-diphenylmethyl-4-[(4-pyrazole)methyl]piperazine.

3C. Formula I Varying -NR¹R²

Similarly, following the procedure of Part A above, but replacing N-(diphenylmethyl)piperazine with:
propylamine;
n-butylamine;
t-butylamine;
hexylamine;
cyclopentylamine;
cyclohexylamine;
adamantadine;
diethylamine;
di-isopropylamine;
dibutylamine;
piperidine;
benzylamine;
phenethylamine;
N-methyl-phenethylamine;
piperazine;
phenylpiperazine;
1-(2-methoxyphenyl)piperazine; and
1-(4-chlorophenyl)piperazine),
there is obtained:
N-propyl-N-[(2-(4-methylphenyl)-5-methyl-1H-imidazol-4-yl)methyl]amine;
N-n-butyl-N-[(2-(4-methylphenyl)-5-methyl-1H-imidazol-4-yl)methyl]amine;
N-t-butyl-N-[(2-(4-methylphenyl)-5-methyl-1H-imidazol-4-yl)methyl]amine;
N-hexyl-N-[(2-(4-methylphenyl)-5-methyl-1H-imidazol-4-yl)methyl]amine;
N-cyclopentyl-N-[(2-(4-methylphenyl)-5-methyl-1H-imidazol-4-yl)methyl]amine;
N-cyclohexyl-N-[(2-(4-methylphenyl)-5methyl-1H-imidazol-4-yl)methyl]amine;
N-adamantyl-N-[(2-(4-methylphenyl)-5-methyl-1H-imidazol-4-yl)methyl]amine;
N-diethyl-N-[(2-(4-methylphenyl)-5-methyl-1H-imidazol-4-yl)methyl]amine;
N-di-isopropyl-N-[(2-(4-methylphenyl)-5-methyl-1H-imidazol-4-yl)methyl]amine;
N-dibutyl-N-[(2-(4-methylphenyl)-5-methyl-1H-imidazol-4-yl)methyl]amine;
N-[(2-(4-methylphenyl)-5-methyl-1H-imidazol-4-yl)methyl]piperidine;
N-benzyl-N-[(2-(4-methylphenyl)-5-methyl-1H-imidazol-4-yl)methyl]amine;
N-phenethyl-N-[(2-(4-methylphenyl)-5-methyl-1H-imidazol-4-yl)methyl]amine;
N-N-methyl-phenethyl-N-[(2-(4-methylphenyl)-5-methyl-1H-imidazol-4-yl)methyl]amine;
1-[(2-(4-methylphenyl)-5-methyl-1H-imidazol-4-ylmethyl]piperazine, alone or mixed with 1,4-di-[(2-(4-methylphenyl)-5-methyl-1H-imidazol-4-yl)methyl]piperazine;
1-phenyl-4-[(2-(4-methylphenyl)-5-methyl-1H-imidazol-4-yl)methyl]piperazine;
1-(2-methoxyphenyl)-4-[(2-(4-methylphenyl)-5-methyl-1H-imidazol-4-yl)methyl]piperazine; and
1-(4-chlorophenyl)-4-[(2-(4-methylphenyl)-5-methyl-1H-imidazol-4-yl)methyl]piperazine).

3D. Formula I Varying -NR¹R²

Similarly, following the procedure of Part A above, but replacing N-(diphenylmethyl)piperazine with:
N-[di-(2-methylphenyl)methyl]piperazine;
N-[di-(3-methylphenyl)methyl]piperazine;
N-[di-(4-methylphenyl)methyl]piperazine;
N-[di-(2-t-butylphenyl)methyl]piperazine;
N-[di-(3-t-butylphenyl)methyl]piperazine;
N-[di-(4-t-butylphenyl)methyl]piperazine;
N-[di-(2-methoxyphenyl)methyl]piperazine;
N-[di-(3-methoxyphenyl)methyl]piperazine;
N-[di-(4-methoxyphenyl)methyl]piperazine;
N-[di-(2-chlorophenyl)methyl]piperazine;
N-[di-(3-chlorophenyl)methyl]piperazine;
N-[di-(4-chlorophenyl)methyl]piperazine;
N-[di-(4-fluorophenyl)methyl]piperazine;
N-benzylpiperazine;
N-[1-(4-chlorophenyl)-1-(phenyl)methyl]piperazine;
N-(2,2-diphenylethyl)piperazine;
N-[3-(phenyl)-3-(4-methoxyphenyl)propyl]piperazine; and
N-(4,4-diphenylbutyl)piperazine,
there is obtained:
1-[di-(2-methylphenyl)methyl]-4-[(2-(4-methylphenyl)-5-methyl-1H-imidazol-4-yl)methyl]piperazine;
1-[di-(3-methylphenyl)methyl]-4-[(2-(4-methylphenyl)-5-methyl-1H-imidazol-4-yl)methyl]piperazine;
1-[di-(4-methylphenyl)methyl]-4-[(2-(4-methylphenyl)-5-methyl-1H-imidazol-4-yl)methyl]piperazine;
1-[di-(2-t-butylphenyl)methyl]-4-[(2-(4-methylphenyl)-5-methyl-1H-imidazol-4-yl)methyl]piperazine;
1-[di-(3-t-butylphenyl)methyl]-4-[(2-(4-methylphenyl)-5-methyl-1H-imidazol-4-yl)methyl]piperazine;
1-[di-(4-t-butylphenyl)methyl]-4-[(2-(4-methylphenyl)-5-methyl-1H-imidazol-4-yl)methyl]piperazine;
1-[di-(2-methoxyphenyl)methyl]-4-[(2-(4-methylphenyl)-5-methyl-1H-imidazol-4-yl)methyl]piperazine;
1-[di-(3-methoxyphenyl)methyl]-4-[(2-(4-methylphenyl)-5-methyl-1H-imidazol-4-yl)methyl]piperazine;
1-[di-(4-methoxyphenyl)methyl]-4-[(2-(4-methylphenyl)-5-methyl-1H-imidazol-4-yl)methyl]piperazine;
1-[di-(2-chlorophenyl)methyl]-4-[(2-(4-methylphenyl)-5-methyl-1H-imidazol-4-yl)methyl]piperazine;
1-[di-(3-chlorophenyl)methyl]-4-[(2-(4-methylphenyl)-5-methyl-1H-imidazol-4-yl)methyl]piperazine;
1-[di-(4-chlorophenyl)methyl]-4-[(2-(4-methylphenyl)-5-methyl-1H-imidazol-4-yl)methyl]piperazine, the trihydrochloride salt of which has a reported melting point of about 225° C.;
1-[di-(4-fluorophenyl)methyl]-4-[(2-(4-methylphenyl)-5-methyl-1H-imidazol-4-yl)methyl]piperazine, the trihydrochloride salt of which has a reported melting point of about 210° C.;
1-benzyl-4-[(2-(4-methylphenyl)-5-methyl-1H-imidazol-4-yl)methyl]piperazine;
1-[1-(4-chlorophenyl)-1-(phenyl)methyl]-4-[(2-(4-methylphenyl)-5-methyl-1H-imidazol-4-yl)methyl]piperazine;
1-(2,2-diphenylethyl)-4-[(2-(4-methylphenyl)-5-methyl-1H-imidazol-4-yl)methyl]piperazine;

1-[3-(phenyl)-3-(4-methyoxyphenyl)propyl]-4-[(2-(4-methylphenyl)-5-methyl-1H-imidazol-4-yl)methyl]-piperazine; and 1-(4,4-diphenylbutyl)-4-[(2-(4-methylphenyl)-5-methyl-1H-imidazol-4-yl)methyl]piperazine.

EXAMPLE 4

1-(2-Methoxyphenyl)-4-[(3-indolyl)methyl]piperazine

4A. Formula I Where Z is 4-[3-(indolyl)methyl], -N-R¹R² is 1-(2-methoxyphenyl)piperazine, and R is Hydrogen One mole (147 g) of indole-3-carbinol and one mole (192 g) of 1-(2-methoxyphenyl)piperazine were dissolved in 1.5 liters of ethanol 60%. One mole (87 g) of lithium bromide and 0.1 mole (5.6 g) of potassium hydroxide were added, then the reaction medium was heated at reflux under stirring for 24 hours. After the reaction medium had cooled to 60° C., hydrochloric acid was added until persistence of an acidic pH. Then 189 g of the dihydrochloride salt of the title product was allowed to crystallize by cooling at 0° C. overnight, producing a global yield of 59% (m.p. 188°-190° C. with decomposition.)

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of making a compound represented by the formula:

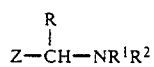

wherein:

Z is a group of the formula HO-AR- where Ar is naphthyl, or phenyl optionally mono-, di-, or tri-substituted, independently, with hydroxy, lower alkyl, lower alkoxy, chloro, or fluoro, or Z is a five to seven membered heterocyclic group of the formula:

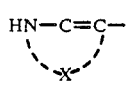

where X is a succession of one or two groups selected from —C=C—, —C=N—, —C=C—C— and —C=N—C—, or Z is a condensed heterocyclic group selected from optionally substituted indole and optionally substituted quinoline;

R is hydrogen, lower alkyl, cyclic lower alkyl, naphthyl, or phenyl optionally mono-, di-, or tri-substituted, independently, with hydroxy, lower alkyl, lower alkoxy, chloro, or fluoro;

R¹ is hydrogen, alkyl, cycloalkyl, naphthyl, or phenyl optionally mono-, di-, or tri-substituted, independently, with hydroxy, lower alkyl, lower alkoxy, chloro, or fluoro;

R² is hydrogen, alkyl, cycloalkyl, naphthyl, or phenyl optionally mono-, di-, or tri-substituted, independently, with hydroxy, lower alkyl, lower alkoxy, chloro, or fluoro;

or NR¹R² taken together forms a heterocycle where R¹ and R² together are lower alkylene of four to six carbon atoms, or lower alkylene of three to five carbon atoms plus one member that is —O—, —S—, or

where R³ is hydrogen, lower alkyl of one to five carbon atoms, cyclic lower alkyl, aryl, arylalkyl or diarylalkyl;

said method comprising reacting a carbinol of the formula:

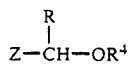

where R⁴ is hydrogen, cycloalkyl, or alkyl;
with a primary or secondary amine of the formula:

in the presence of a cationic effect reagent.

2. The method of claim 1 wherein said cationic effect reagent is a mixture of an alkaline hydroxide with a metal salt.

3. The method of claim 2 wherein said alkaline hydroxide is a potassium or sodium hydroxide.

4. The method of claim 2 wherein said metal salt is a lithium halide or a lithium perchlorate.

5. The method of claim 4 wherein said metal salt is a lithium halide.

6. The method of claim 5 wherein said lithium halide is lithium bromide.

7. The method of claim 6 wherein said alkaline hydroxide is a potassium or sodium hydroxide.

8. The method of claim 7 wherein the ratio said alkaline hydroxide and said metal salt is from 1:20 to 20:1.

9. The method of claim 8 wherein the ratio of said alkaline hydroxide to said metal salt is 0.1:1, and said metal salt is present in an equimolar amount as compared to said carbinol and said primary or secondary amine.

10. The method of claim 1 wherein said reaction is conducted in a medium in which said starting materials are soluble, but in which said final product is insoluble.

11. The method of claim 10 wherein said reaction medium is:

homogenous, selected from hydroalcoholic mixtures and organic solvents, or heterogeneous, selected from a mixture of an aqueous solvent and an aromatic or an aliphatic solvent.

12. The method of claim 10 wherein said aromatic solvent is selected from benzene, toluene and xylene, and said aliphatic solvent is selected from dichloromethane and dichloroethane.

13. The method of claim 11 wherein said reaction medium is a two phase aqueous and organic mixture, in a ratio from 1:10 to 10:1 v/v.

14. The method of claim 10 wherein said reaction medium is a non-aqueous medium.

15. The method of claim 14 wherein said reaction medium is toluene.

16. The method of claim 1, comprising the additional step of heating the reaction mixture to reflux for a period of from 1 to 48 hours.

17. The method of claim 1 wherein said carbinol has a conjugate structure with an acidic character.

18. The method of claim 17 wherein said carbinol is selected from the group consisting of: substituted or unsubstituted hydroxy-phenyl carbinols, 6-hydroxy-2-naphthyl-carbinols and heterocyclic carbinols.

19. The method of claim 18 wherein said carbinol is a substituted or unsubstituted hydroxy-phenyl carbinols, selected from the group consisting of: 2-hydroxybenzyl alcohol, 3-hydroxybenzyl alcohol, 4-hydroxybenzyl alcohol, 4-hydroxy-3-methoxybenzyl alcohol and 4-hydroxy-3-methoxybenzyl alcohol.

20. The method of claim 18 wherein said carbinol is a heterocyclic carbinol, selected from the group consisting of: 2-imidazolyl-carbinols, 3-indolyl-carbinols, and 4-pyrazolyl-carbinols.

21. The method of claim 1 wherein said amine is selected from the group consisting of: primary aliphatic amines, secondary aliphatic amines, arylamines, primary aralkylamines, secondary aralkylamines, optionally substituted piperazines and diphenylmethyl-piperazines.

22. A method making a compound represented by the formula:

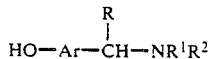

wherein:
Ar is naphthyl, or phenyl optionally mono-, di-, or tri-substituted, independently, with hydroxy, lower alkyl, lower alkoxy, chloro, or fluoro;
R is hydrogen, lower alkyl, cyclic lower alkyl, napthyl, or phenyl optionally mono-, di-, or tri-substituted, independently, with hydroxy, lower alkyl, lower alkoxy, chloro, or fluoro;
$R^1$ is hydrogen, alkyl, cycloalkyl, napthyl, or phenyl optionally mono-, di-, or tri-substituted, independently, with hydroxy, lower alkyl, lower alkoxy, chloro, or fluoro;
$R^2$ is hydrogen, alkyl, cycloalkyl, napthyl, or phenyl optionally mono-, di-, or tri-substituted, independently, with hydroxy, lower alkyl, lower alkoxy, chloro, or fluoro;
or $NR^1R^2$ taken together forms a heterocycle where $R^1$ and $R^2$ together are lower alkylene of four to six carbon atoms, or lower alkylene of three to five carbon atoms plus one member that is —O—, —S—, or

where $R^3$ is hydrogen, lower alkyl of one to five carbon atoms, cyclic lower alkyl, aryl, arylalkyl or diarylalkyl;

said method comprising reacting a hydroxy aryl carbinol of the formula:

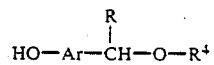

where $R^4$ is hydrogen, cycloalkyl, or alkyl;
with a primary or secondary amine of the formula:

in the presence of a cationic effect reagent.

23. A method of making a compound represented by the formula:

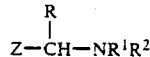

wherein:
Z is a five to seven membered heterocyclic group of the formula:

where X is a succession of one or two groups selected from —C=C—, —C=N—, —C=C—C— and —C=N—C—, or
Z is a condensed heterocyclic group selected from optionally substituted indole and optionally substituted quinoline;
R is hydrogen, lower alkyl, cyclic lower alkyl, napthyl, or phenyl optionally mono-, di-, or tri-substituted, independently, with hydroxy, lower alkyl, lower alkoxy, chloro, or fluoro;
$R^1$ is hydrogen, alkyl, cycloalkyl, napthyl, or phenyl optionally mono-, di-, or tri-substituted, independently, with hydroxy, lower alkyl, lower alkoxy, chloro, or fluoro;
$R^2$ is hydrogen, alkyl, cycloalkyl, napthyl, or phenyl optionally mono-, di-, or tri-substituted, independently, with hydroxy, lower alkyl, lower alkoxy, chloro, or fluoro;
or $NR^1R^2$ taken together forms a heterocycle where $R^1$ and $R^2$ together are lower alkylene of four to six carbon atoms, or lower alkylene of three to five carbon atoms plus one member that is —O—, —S—, or

where $R^3$ is hydrogen, lower alkyl of one to five carbon atoms, cyclic lower alkyl, aryl, arylalkyl or diarylalkyl;
said method comprising reacting a heterocyclic carbinol of the formula:

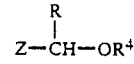

where $R^4$ is hydrogen, cycloalkyl, or alkyl;
with a primary or secondary amine of the formula:

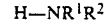

in the presence of a cationic effect reagent.

* * * * *

UNITED STATES PATENT AND TRADEMARK OFFICE
CERTIFICATE OF CORRECTION

PATENT NO. : 5,142,052

DATED : August 25, 1992

INVENTOR(S) : Beranger, et al.

It is certified that error appears in the above-identified patent and that said Letters Patent is hereby corrected as shown below:

Claim 1, at column 13, lines 61-62 "optionally substituted indole and optionally substituted quinoline" should read --indole and quinoline--.

Claim 23, at column 16, lines 23-25 the formula
"HN-C=C-"   should read   --HN-C=C- --
        |                          |   |
        X                          ·.X.· and at column 16, lines 31-32 "optionally substituted indole and optionally substituted quinoline" should read --indole and quinoline--.

Signed and Sealed this

Twenty-eighth Day of September, 1993

Attest:

BRUCE LEHMAN

*Attesting Officer*          *Commissioner of Patents and Trademarks*